United States Patent
Tes et al.

(10) Patent No.: US 8,066,013 B2
(45) Date of Patent: Nov. 29, 2011

(54) INSTRUMENT FOR PEDICURE

(76) Inventors: Sentrakal Tes, Effort, PA (US); Malen Chea, Effort, PA (US)

( * ) Notice: Subject to any disclaimer, the term of this patent is extended or adjusted under 35 U.S.C. 154(b) by 584 days.

(21) Appl. No.: 12/133,921

(22) Filed: Jun. 5, 2008

(65) Prior Publication Data
US 2009/0301507 A1 Dec. 10, 2009

(51) Int. Cl.
*A45D 29/05* (2006.01)
(52) U.S. Cl. ......................................................... 132/73.6
(58) Field of Classification Search ................ 132/73, 132/73.5, 73.6, 75.3, 75.6, 75.8, 76.4; 451/356, 451/359, 910
See application file for complete search history.

(56) References Cited

U.S. PATENT DOCUMENTS

| | | | |
|---|---|---|---|
| 4,520,938 A | 6/1985 | Finke | |
| 5,462,182 A | 10/1995 | Opresco | |
| 5,562,218 A | 10/1996 | Hamilton et al. | |
| 6,331,744 B1 | 12/2001 | Chen et al. | |
| 6,470,895 B1 | 10/2002 | Miller et al. | |
| 6,523,546 B2 | 2/2003 | Jo et al. | |
| 6,760,945 B2 | 7/2004 | Ferber et al. | |
| 6,798,169 B2 | 9/2004 | Stratmann et al. | |
| 6,906,495 B2 | 6/2005 | Cheng et al. | |
| 7,347,211 B1 | 3/2008 | Macklin | |
| 7,581,545 B1 * | 9/2009 | Moldawski et al. | 132/76.4 |
| 2002/0050278 A1 * | 5/2002 | Jo et al. | 132/73.6 |
| 2006/0122631 A1 * | 6/2006 | Kertz | 606/131 |
| 2006/0176017 A1 | 8/2006 | Waguespack | |
| 2006/0272664 A1 * | 12/2006 | O'Dwyer | 132/73.6 |
| 2007/0221238 A1 | 9/2007 | Tran | |
| 2007/0293795 A1 * | 12/2007 | Carroll | 601/138 |

FOREIGN PATENT DOCUMENTS
JP 2000189235 A2 7/2000

OTHER PUBLICATIONS http://www.amazon.com/gp/product/images/B0008ENT9C/ref=dp_image_text_0?ie=UTF88n=37609018s=hpc.
http://akamai.globalsources.com.edgesuite.net/f/593/3445/5d/pdt.static.globalsources.com/IMAGE.
http://www.usalifestyle.net/theproducts.cfm?master=7677&owner=651.
http://www.clearpointdirect.com/proddetail.php-?prod=1109000000.
http://us.st11.yimg.com/us.st.yimg.com/brandsonsale-store_1986_224788205.
Schurman, Kyle, "Fulton Innovation's Intelligent Wireless Power Cutting the Cords With eCoupled," Computer Power User.
International Search Report with respect to International Application No. PCT/US2009/042262.

* cited by examiner

*Primary Examiner* — Rachel Steitz
(74) *Attorney, Agent, or Firm* — Caesar Rivise; Bernstein Cohen & Pokotilow, Ltd.

(57) ABSTRACT

A hand-held electronic pedicure instrument includes a housing having an outside portion and an inside portion. The inside portion includes a battery electrically coupled to a motor which can be activated by a switch on the outside portion of the housing. The outside portion of the housing also has a handle. The motor provides rotational output to a shaft extending from the inside portion of the housing, through an opening in the housing and beyond the outside portion of the housing, the shaft having a distal end. The instrument further has a wheel having proximal and distal surfaces. The distal end of the shaft secures to the proximal surface of the wheel. An attachment has a proximal portion that is removably secured to the distal surface of the wheel. The attachment has a distal portion having an abrasive material.

3 Claims, 3 Drawing Sheets

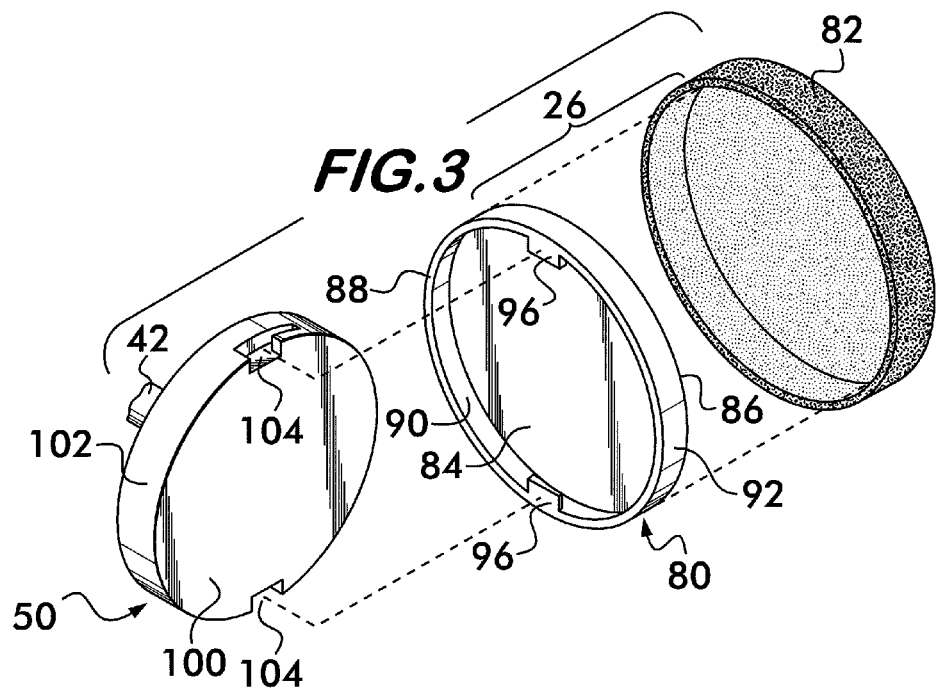
*FIG.3*
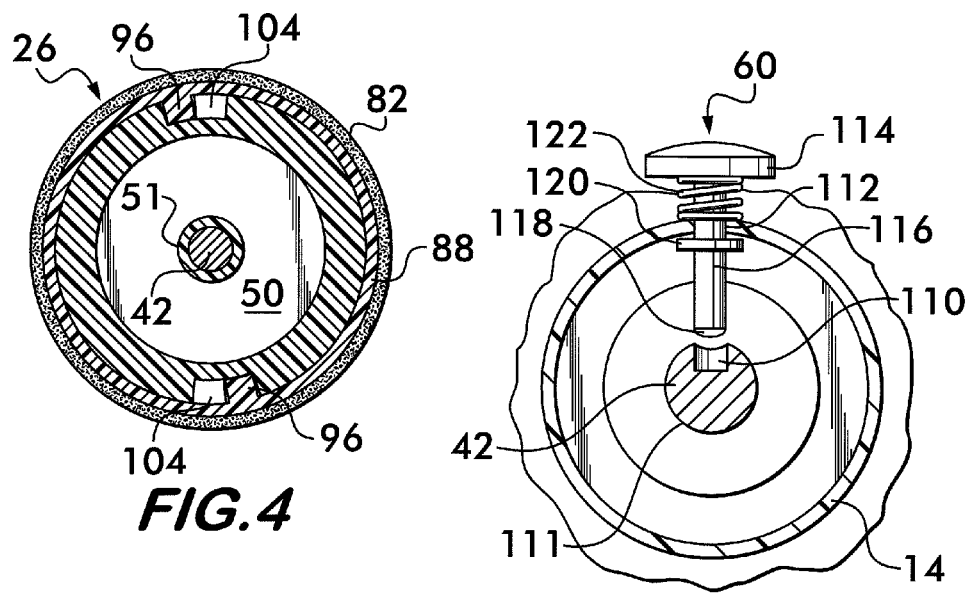
*FIG.4*
*FIG.5*

INSTRUMENT FOR PEDICURE

BACKGROUND OF THE INVENTION

1. Field of Invention

This invention relates to an electronic pedicure instrument used for care and treatment of the hands or feet, including removal of calluses or corns from the feet or hands.

2. Description of Related Art

During a pedicure, calluses, corns and dry, dead, or flaky skin (hereinafter, collectively, "skin imperfections") are abraded or scraped from the bottom of the feet. This process is optimally performed after the foot has soaked in warm water. Various tools known in the art for removal of skin imperfections include pedicure sanders, callus rasps, pumice stones, pumice sponges and/or razors. Although razors are often very effective for this purpose, they carry a risk of injury. In fact, many states in the United States of America have passed laws prohibiting the commercial use of razors in performing pedicures, and it is expected that more states will follow suit.

The manual performance of a pedicure with abrasive tools, e.g., pumice sponges, is tedious and can result in significant fatigue to the pedicurist, especially when the pedicurist performs several pedicures per day. Some pedicurists experience pain and unfortunately even physical impairments, e.g., carpal tunnel syndrome, from repeated use of manually operated abrasive pedicure tools.

Accordingly, attempts have been made to automate the process of removing skin imperfections from the feet and hands. For example, Jerdon Products, LLC sells a battery-powered pedicure instrument under the name "Pedi-Smooth" and product number JD51BX. This instrument is powered by three AA batteries and comes with detachable rotary sandpaper refills. The sandpaper refills provide an abrasive surface for performance of the pedicure. However, the Pedi-Smooth does not operate at sufficient revolutions per minute (RPM) to adequately remove skin imperfections. It is therefore not popularly used commercially by pedicurists.

U.S. Pat. No. 6,523,546 (Jo) discloses a pedicure sander used for removing calluses or corns from the feet. The sander comprises a motor-driven cylindrical abrasive rotary body. The rotary body and motor are located within a housing. The housing has at least one opening exposing a portion of the rotary body in order to allow the rotary body to contact the skin during a pedicure. Although an improvement over manual tools for the removal of skin imperfections, the structure of this device is not conducive to comfortable use, and can cause undue stress to the hand and wrist of a pedicurist who uses it for extended periods of time throughout the day. The device is not characterized in Jo as being water-tight, and therefore can be unsafe to use in wet environments (in which pedicures are typically performed). The device is capable of providing rotary motion to the cylindrical rotary body at varied RPM. However Jo does not mention the RPM at which the device operates - a parameter which is essential to the effective removal of skin imperfections. Additionally, the cylindrical rotary body is not removable and replaceable. Thus, wear over time as well as collection of bacteria through use can diminish the safety and effectiveness of the device.

U.S. Pat. Pub. No. 20070221238 (Tran) discloses a foot sanding disk adapted to attach to an output shaft of a motorized rotary tool. The details of a rotary tool onto which the disk would attach are not disclosed in Tran. The abrasive materials disclosed for use with the disk, e.g., silica, garnet, silicon carbide, and aluminum oxide, are not ideal for the removal of skin imperfections.

What is therefore needed is a safe and effective electronic pedicure instrument for the removal of skin imperfections. The instrument can be suitable for commercial or home use. Additionally, the instrument would preferably be cordless, rechargeable, safe for use in wet environments and comfortable to use over extended periods of time.

BRIEF SUMMARY OF THE INVENTION

Accordingly, a hand-held electronic pedicure instrument is provided, comprising an instrument housing having an outside portion and an inside portion. The inside portion includes a motor and a battery, the battery being electrically coupled to the motor which can be activated by a switch located on the outside portion of the instrument housing. The outside portion of the instrument housing also has a handle.

The motor provides rotational output to an output shaft extending proximally from the inside portion of the instrument housing, distally through an opening in the instrument housing and beyond the outside portion of the instrument housing. The output shaft has an outer surface and a distal end.

The instrument further includes a wheel having a proximal surface, a distal surface and a central axis. The distal end of the output shaft is secured to the proximal surface of the wheel along the central axis of the wheel. An attachment is also provided, having a proximal portion and a distal portion. The distal portion of the attachment has an abrasive material. The proximal portion of the attachment is removably secured to the distal surface of the wheel.

BRIEF DESCRIPTION OF SEVERAL VIEWS OF THE DRAWINGS

The invention will be described in conjunction with the following drawings in which like reference numerals designate like elements and wherein:

FIG. 3 is an exploded view of an abrasive attachment and wheel according to the present invention.

FIG. 4 is a sectional view of the abrasive attachment and wheel along section line 4-4 of FIG. 2.

FIG. 5 is a partial sectional view along section line 5-5 of FIG. 2 showing in detail a depressible pin system according to the present invention.

DETAILED DESCRIPTION OF THE INVENTION

Figure 1:
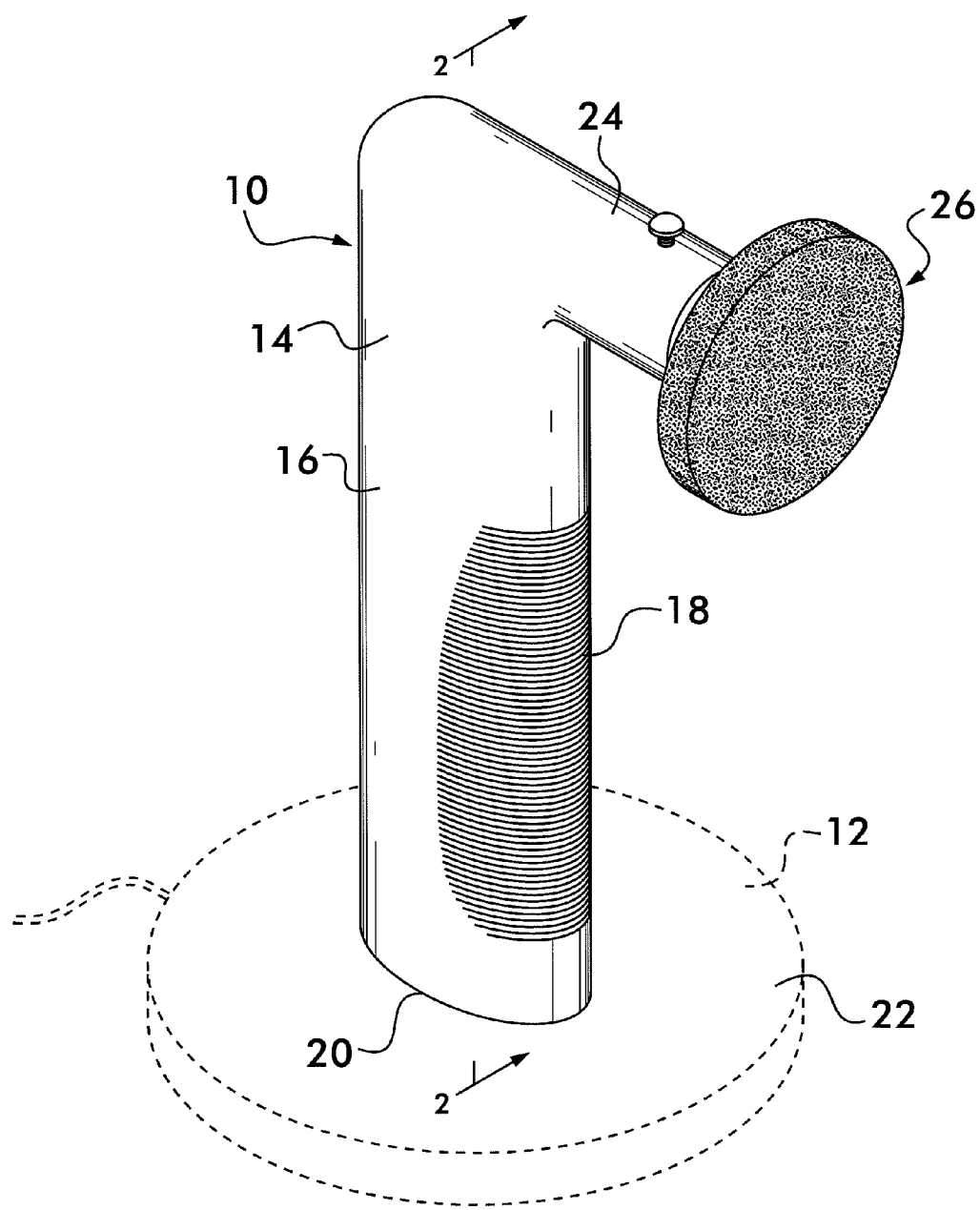
FIG. 1 is an isometric view of an electronic pedicure instrument according to the present invention mounted atop a battery charging base.

Referring now in detail to the various figures of the drawings wherein like reference characters refer to like parts, there is shown in FIG. 1 an isometric view of an electronic pedicure instrument 10 according to the present invention, mounted atop a battery charging base 12.

The instrument 10 has a housing 14 which is preferably watertight, in order to prevent various electrical components located within the housing from coming into contact with water. It is preferred that the housing 14 be made out of plastic, although other materials, e.g., metal or rubber may be used as well.

The outside portion of the housing 14 includes a handle 16 having a grip 18 on its front. The grip 18 helps a user to maintain a firm grasp on the instrument 10 and prevents the instrument 10 from accidentally slipping from the user's hand. The grip 18 is preferably rubberized, however it can also comprise a machined or molded pattern on the outside portion of the housing 14. At the bottom of the handle 16 is its base 20, which, as shown in FIG. 1, rests on the top surface 22 of the battery charging base 12.

The housing 14 further includes a neck 24, which extends distally, at a right angle from the handle 16. In alternative embodiments (not shown), the neck 24 may extend distally from the handle 16 at an angle greater than 90° and up to 180° from the handle 16. Extending distally from the neck 24 is a removable rotary abrasive attachment 26 which effectuates the removal of skin imperfections from, e.g., a person's feet or hands.

Figure 2:
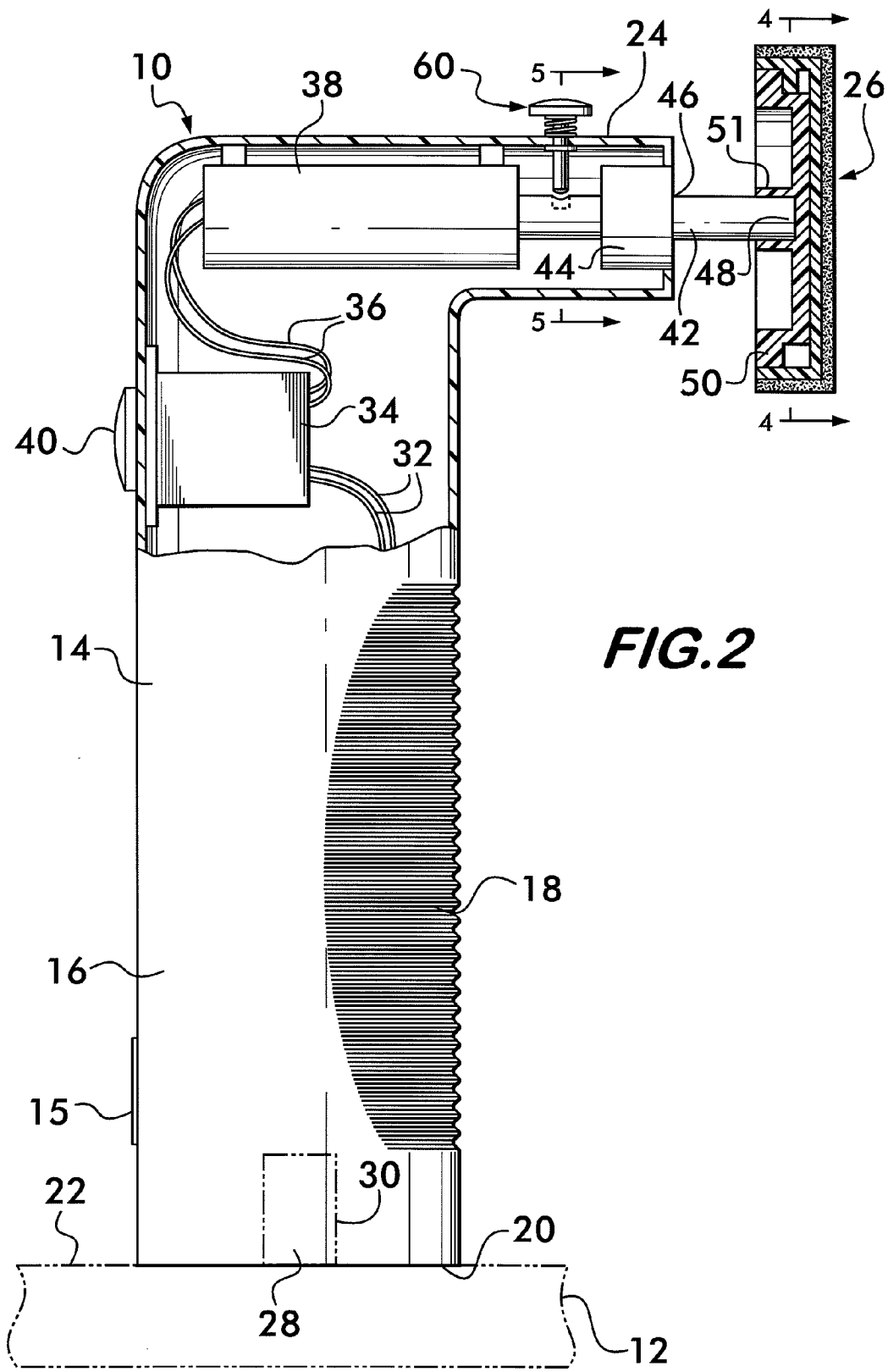
FIG. 2 is a partial sectional view of the electronic pedicure instrument shown in FIG. 1 along line 2-2.

Referring now to FIG. 2, there is shown a partial sectional view of the instrument 10 of FIG. 1 along section line 2-2. As shown in FIG. 2, the battery charging base 12 includes a vertical charging post 28 which mates with the female charging receptor 30 so as to provide power for storage in a rechargeable battery, or batteries (not shown) located within the handle 16. The battery or batteries preferably provide electric potential in the amount of 7.2V or 9.0V. The charging post 28 and female charging receptor 30, can respectively include coils within them (not shown) which operate to transfer power to the battery via inductive coupling. The mechanism of inductive coupling to be used in the present invention as a means for "contactless" recharging is described in U.S. Pat. No. 6,331,744 (Chen), U.S. Pat. No. 6,798,169 (Stratmann) and *White Paper: Fulton Innovation's Intelligent Wireless Power*, Computer Power User, Vol. 7 Issue 5, at pp. 54-57 (May 2007), which are incorporated by reference herein in their entireties. On the rear of the handle 16 is a charging indicator 15, which lights up, flashes and/or changes color once the battery is charged.

"Contactless" recharging, e.g., through inductive coupling, is most preferred because it helps to maximize safe use of the instrument 10 in and around water. However, the instrument 10 according to the present invention may be powered or charged in other ways. For example, its batteries may be charged by conductive charging or direct coupling, e.g., through the use of charging connectors such as those described in U.S. Pat. App. Pub. No. 2006/0176017 (Waguespack), which is incorporated by reference herein in its entirety. Alternatively, the instrument may use batteries that are not rechargeable. Still yet, it may not use batteries at all, but rather, be powered by connecting a power cord directly to an electric socket.

Still referring to FIG. 2, the batteries (not shown) are electrically coupled via first electrical leads 32 to encased switch electronics 34, which are, in turn, electrically coupled via second electrical leads 36 to a DC motor 38. The batteries (not shown) thereby provide power to the motor 38. A switch 40 located on the outside portion of the housing 14 interfaces with the switch electronics 34 to effectuate activation and deactivation of the motor 38. The switch 40 is preferably a 2-way or 3-way switch capable of providing variable power to the motor 38.

When activated, the motor 38 provides rotational motion to an output shaft 42. The output shaft 42 extends from the motor 38 through a journal 44, and distally through a preferably watertight opening 46 in the neck 24 of the housing 14. The output shaft 42, which has a distal end 48, extends beyond the outside portion of the housing 14. A cylindrical wheel 50 made out of a suitable material, e.g., metal or plastic, is secured at its hub 51 to the distal end 48 of the output shaft 42. The wheel 50 is preferably rigidly secured to the distal end 48 of the output shaft 42, although in an alternative embodiment, the wheel 50 may be removably secured thereto. Either way, since the wheel 50 is rotationally driven by the output shaft 42, the wheel 50 must be securely locked in place onto the output shaft, i.e., unable to rotate independently of the output shaft 42.

The rotary abrasive attachment 26 is removably secured to the wheel 50. In its various embodiments, as explained in further detail infra, a user would attach or remove the abrasive attachment 26 to/from the wheel 50 by slightly rotating the attachment 26 onto/off of the wheel 50. During this process, the wheel 50 and output shaft 42 must be stationary, ie., prevented from rotating. This may be achieved, for example, with the depressible pin system 60, the operation of which is explained in detail, infra.

Referring now to FIG. 3, there is shown an exploded view of the abrasive attachment 26 in its component parts, i.e., the cap 80 and abrasive material 82. In its manufactured form, the abrasive attachment 26 is one unit, the cap 80 and abrasive material 82 being permanently secured to one another, e.g., by glue or another permanent adhesive.

The abrasive material 82 is preferably synthetic pumice sponge or pumice stone. Synthetic pumice sponge or pumice stone are the most effective materials for the safe removal of skin imperfections. Moreover, such materials often have antibacterial properties, which are beneficial to a person receiving a pedicure and preserve the life of the abrasive material 82. Particularly preferred pumice sponges for the abrasive material 82 are those produced in Germany by TITANIA®, as well as those sold under the names Pumice King™ and Mr. Pumice™. The abrasive material 82 can alternatively be made of other abrasives used in the art, such as sand paper, natural pumice sponge or natural pumice stone. Whichever abrasive material 82 is used, it should be capable of safely and effectively removing skin imperfections.

The cap 80 has a proximal surface 84 and a distal surface 86. The cap 80 can further include a rim 88 having an inner surface 90 and an outer surface 92. The inner surface 90 of the rim 88 includes two tapered protrusions 96 located opposite one another. As shown in FIGS. 1-3, the abrasive material 82 covers the entire distal surface 86 of the cap 80 as well as the entire outer surface 92 of the rim 88. Although it is preferred that these surfaces be entirely covered by the abrasive material 82, there may be embodiments of the abrasive attachment 26 according to the present invention in which these surfaces are not entirely covered. For example, in an alternative embodiment (not shown) of the abrasive attachment 26, the distal surface 86 is entirely covered by abrasive material 82, but the outer surface 92 of the rim 88 is not.

As shown in FIG. 3, the wheel 50 comprises a distal surface 100 and sidewall 102. The wheel 50 further includes two tapered slots 104 located opposite one another, where the distal surface 100 and sidewall 102 intersect. The tapered slots 104 of the wheel 50 are sized to securely mate with the tapered protrusions 96 of the cap 80. When a user wishes to secure the abrasive attachment 26 to the wheel 50, the user first aligns the tapered protrusions 96 with the tapered slots 104. Next, the user presses the abrasive attachment 26 against the wheel 50, thereby inserting the tapered protrusions 96 into the tapered slots 104. Lastly, the user slightly rotates the abrasive attachment 26 clockwise while the wheel 50 is stationary, in order to securely mate the tapered protrusions 96 with the tapered slots 104, thereby securing the abrasive attachment 26 to the wheel 50.

FIG. 4, which is a sectional view along line 4-4 of FIG. 2, shows the abrasive attachment 26 secured to the wheel 50, the tapered protrusions 96 securely mated with the tapered slots 104 as described supra.

When the instrument 10 is in use, the wheel 50 rotates counterclockwise, i.e., opposite the direction that the abrasive attachment 26 is rotated when secured onto the wheel 50. In this way, the operation of the instrument 10 effectively forces the tapered protrusions 96 to maintain a strong interlock with the tapered slots 104. Additionally, as shown in FIGS. 3 and 4, the tapered slots 104 prevent translational movement of the abrasive attachment 26 relative to the wheel 50, when the tapered protrusions 96 are securely mated with the tapered slots 104. In this way, the abrasive attachment 26 will not be unintentionally detached from the wheel 50 when the instrument 10 is in use.

In order to remove the abrasive attachment 26 from the wheel 50, the user first slightly rotates the abrasive attachment 26 counterclockwise while the wheel 50 is stationary, thereby unfastening the tapered protrusions 96 from the tapered slots 104. Next, the user pulls the abrasive attachment 26 away from the wheel 50, thereby removing the abrasive attachment 26.

The removability of the abrasive attachment 26 is a preferred feature. Through use, the abrasive attachment 26 becomes worn and in need of replacement. In a commercial setting, e.g., a salon, a pedicurist would potentially use the instrument 10 on many different people per day. For sanitary reasons, the same abrasive attachment 26 should not be used on more than one person. The abrasive attachment 26 should therefore be quickly and easily removable from, and securable to, the wheel 50, preferably without tools or additional components (e.g., screws) for effectuating removal and attachment.

The cap 80 and wheel 50 according to the present invention are not limited to the structures described supra. Rather, the invention includes many alternative embodiments in which those components could be quickly and easily attached and separated. For example, in one embodiment (not shown), the inner surface 90 of the rim 88 is threaded, as is the sidewall 102 of the wheel 50. In that embodiment, the cap 80 could simply be screwed onto the wheel 50.

In another embodiment the cap 80 and the wheel 50 are oppositely charged magnets. When mated together, the magnetic force between the cap 80 and the wheel 50 holds the two components together, preventing them from being unintentionally pulled apart. The cap 80 and wheel 50 further include mating geometry in their respective contacting surfaces which prevents rotational movement between those two components.

In yet another embodiment (not shown), the cap 80 and wheel 50 engage with and disengage from one another, as do any of the child-resistant medicine bottles and caps, such as those described in U.S. Pat. No. 5,462,182 (Opresco), U.S. Pat. No. 4,520,938 (Finke) and U.S. Pat. No. 5,562,218 (Hamilton), which are incorporated herein by reference in their entireties.

As mentioned supra, the wheel 50 should be prevented from rotating while the abrasive attachment 26 is being secured to, or removed from it. This could be accomplished manually, e.g., by physically holding the wheel 50 and/or output shaft 42 in place. However, it is preferred that the instrument 10 include a built-in mechanical means for a user to prevent the wheel 50 from rotating while removing and securing the abrasive attachment 26. Such means may be embodied in a variety of ways, one of which is shown in detail in FIG. 5.

FIG. 5, which is a partial sectional view along section line 5-5 of FIG. 2, shows a depressible pin system 60 according to the present invention. The depressible pin system 60 includes a head 114 with a shank 116 extending therefrom, the shank 116 having a bottom end 118 located opposite the head 114. A flange 120 is rigidly secured around the shank 116 at a position between the head 114 and the bottom end 118 of the shank 116. The shank 116 fits through a small hole 112 in the instrument housing 14, the flange 120 being located within the instrument housing 14. The flange 120 is unable to fit through the small hole 112 and therefore operates as a stop to prevent the shank 116 from being completely removed from the housing 14.

The outer surface 111 of the output shaft 42 has a notch 110 which is adapted to receive the bottom end 118 of the shank 116. The small hole 112 in the housing 14, as well as the shank 116, are substantially lined up with the notch 110. A compression spring 122 is fitted around the shank 116 between the head 114 and the outside portion of the instrument housing 14. The compression spring 122 forces the head 114 away from the housing 14 when there is no counteracting force, e.g., from a user's thumb, applied to the top of the head 114. This way, when the instrument 10 is in use, there is space between the bottom end 118 of the shank 116 and the output shaft 42, so that the shank 116 does not interfere with the rotating output shaft 42.

To use the depressible pin system 60, a user applies pressure, e.g., with his or her thumb, to the top of the head 114, slightly rotating the wheel 50 until the bottom end 118 of the shank 116 is received by, and securely mates with, the notch 110. By continuing to maintain pressure to the top of the head 114, the output shaft 42, and consequently the wheel 50, are effectively prevented from rotating. It is in this state that the abrasive attachment 26 can be removed from, or secured onto, the wheel 50.

As discussed supra, a drawback of prior art electronic pedicure devices is that they do not rotate at sufficient RPM to effectively remove skin imperfections from, e.g., feet or hands. It is therefore preferred that the motor 38 provide sufficient rotational speed to the output shaft 42 to achieve this purpose. Preferably, the abrasive attachment 26 would rotate at between 4,000 to 8,000 RPM. More preferably, the switch 40 would have at least two separate settings for operating the motor 38, e.g., a "low" setting and a "high" setting. Activating the switch 40 in the "low" setting may, for example, cause the motor 38 to operate at 5,000 RPM. Activating the switch 40 in the "high" setting may, for example, cause the motor to operate at 7,500 RPM.

While the invention has been described in detail and with reference to specific examples thereof, it will be apparent to one skilled in the art that various changes and modifications can be made therein without departing from the spirit and scope thereof.

What is claimed is:

1. A hand-held electronic pedicure instrument comprising:
   a. a watertight instrument housing having an outside portion and an inside portion, the inside portion including a motor and a battery which is rechargeable and is charged by contactless inductive coupling from a recharging base, the battery being electrically coupled to the motor which can be activated by a switch located on the outside portion of the instrument housing, the outside portion of the instrument housing having a handle;
   b. the motor providing rotational output to an output shaft extending proximally from the inside portion of the instrument housing, distally through an opening in the instrument housing and beyond the outside portion of the instrument housing, the output shaft having an outer surface and a distal end, wherein the motor produces a rotational output range of 4000 to 8000 revolutions per minute;

c. a wheel having a proximal surface, a distal surface and a central axis, the distal end of the output shaft being secured to the proximal surface of the wheel along the central axis of the wheel;

d. an attachment having a distal portion having an abrasive material comprising pumice sponge or pumice stone and a proximal portion being removably secured to the distal surface of the wheel; and e. a depressible pin system to prevent rotation of the output shaft, the output shaft having a notch in its outer surface within the inside portion of the instrument housing, the instrument housing having a small hole substantially lined up with the notch, the depressible pin system comprising a head with a shank extending therefrom, the shank having a bottom end located opposite the head, a flange rigidly secured around the shank at a point between the head and the bottom end, wherein the shank fits through the small hole such that the flange is located within the inside portion of the instrument housing and is unable to fit though the small hole so as to effectively prevent the shank from being completely removed from the instrument housing, the bottom end of the shank being adapted to securely fit within the notch such that, when pressure is applied to the head towards the instrument housing, the bottom end of the shank fits within the notch thereby preventing the output shaft from being able to rotate, the depressible pin system further comprising a compression spring fitted around the shank between the head and the outside portion of the instrument housing.

2. A hand-held electronic pedicure instrument comprising:

a. a watertight instrument housing having an outside portion and an inside portion, the inside portion including a motor and a battery which is rechargeable and is charged by contactless inductive coupling from a recharging base, the battery being electrically coupled to the motor which can be activated by a switch located on the outside portion of the instrument housing, the outside portion of the instrument housing having a handle;

b. the motor providing rotational output to an output shaft extending proximally from the inside portion of the instrument housing, distally through an opening in the instrument housing and beyond the outside portion of the instrument housing, the output shaft having an outer surface and a distal end, wherein the motor produces a rotational output range of 4000 to 8000 revolutions per minute;

c. a wheel having a proximal surface, a distal surface and a central axis, the distal end of the output shaft being secured to the proximal surface of the wheel along the central axis of the wheel; and d. an attachment having a distal portion having an abrasive material comprising pumice sponge or pumice stone and a proximal portion being removably secured to the distal surface of the wheel, wherein the wheel comprises at least two slots and the attachment comprises at least two protrusions insertable into and securable within the slots, the attachment being securable to the wheel by pressing the attachment against the wheel such that the protrusions are inserted into the slots, and then, while the wheel is stationary, rotating the attachment relative to the wheel in a direction opposite the direction of rotational output of the output shaft, thereby securing the protrusions within the slots and the attachment to the wheel, the attachment being removable from the wheel by, while the wheel is stationary, rotating the attachment relative to the wheel in the same direction as the direction of rotational output of the output shaft, and then pulling the attachment away from the wheel thereby removing the attachment from the wheel.

3. A hand-held electronic pedicure instrument comprising:

a. a watertight instrument housing having an outside portion and an inside portion, the inside portion including a motor and a battery which is rechargeable and is charged by contactless inductive coupling from a recharging base, the battery being electrically coupled to the motor which can be activated by a switch located on the outside portion of the instrument housing, the outside portion of the instrument housing having a handle;

b. the motor providing rotational output to an output shaft extending proximally from the inside portion of the instrument housing, distally through an opening in the instrument housing and beyond the outside portion of the instrument housing, the output shaft having an outer surface and a distal end, wherein the motor produces a rotational output range of 4000 to 8000 revolutions per minute;

c. a wheel having a proximal surface, a distal surface and a central axis, the distal end of the output shaft being secured to the proximal surface of the wheel along the central axis of the wheel; and d. an attachment having a distal portion having an abrasive material comprising pumice sponge or pumice stone and a proximal portion being removably secured to the distal surface of the wheel, the attachment further comprising a proximal portion, the proximal portion of the attachment and distal surface of the wheel being magnetized at opposite charges such that when pressed together, magnetic forces resist separation of the attachment from the wheel, the proximal portion of the attachment and distal surface of the wheel further comprising complementary mating geometries which prevent rotational movement between the attachment and the wheel when the geometries are mated with one another.

* * * * *